(12) United States Patent
Zacharias

(10) Patent No.: US 8,881,579 B2
(45) Date of Patent: Nov. 11, 2014

(54) METHOD AND DEVICE FOR DETERMINING VISCOSITY UTILIZING GRAVITY FEED

(75) Inventor: Joerg Zacharias, Koefering (DE)

(73) Assignee: Krones AG, Neutraubling (DE)

( * ) Notice: Subject to any disclaimer, the term of this patent is extended or adjusted under 35 U.S.C. 154(b) by 377 days.

(21) Appl. No.: 13/198,820

(22) Filed: Aug. 5, 2011

(65) Prior Publication Data

US 2012/0031173 A1    Feb. 9, 2012

(30) Foreign Application Priority Data

Aug. 6, 2010   (DE) .......................... 10 2010 039 031

(51) Int. Cl.
*G01N 11/10* (2006.01)
*G01N 11/00* (2006.01)
*G01N 11/08* (2006.01)

(52) U.S. Cl.
CPC ..................................... *G01N 11/08* (2013.01)
USPC .......................... 73/54.39; 73/54.01; 73/54.02

(58) Field of Classification Search
CPC ...................................................... G01N 11/00
USPC ................................................................ 73/54.02
See application file for complete search history.

(56) References Cited

U.S. PATENT DOCUMENTS

| | | | | |
|---|---|---|---|---|
| 3,494,217 | A | * | 2/1970 | Tatsuo et al. .................. 73/865.5 |
| 3,520,179 | A | | 7/1970 | Reed |
| 4,137,754 | A | * | 2/1979 | Colombo et al. ............. 73/54.11 |
| 4,188,967 | A | * | 2/1980 | Joyce ................................ 137/1 |
| H000093 | H | * | 7/1986 | Matta et al. ................... 73/54.11 |
| 4,641,535 | A | * | 2/1987 | Malguarnera ............... 73/861.01 |
| 5,315,863 | A | * | 5/1994 | Cowper ........................ 73/54.09 |
| 5,847,268 | A | * | 12/1998 | Ball .............................. 73/54.09 |
| 6,134,950 | A | * | 10/2000 | Forster et al. ................ 73/54.01 |
| 6,386,016 | B1 | | 5/2002 | Gleissle |
| 6,412,337 | B1 | * | 7/2002 | Arzate et al. ................. 73/54.09 |
| 6,428,488 | B1 | * | 8/2002 | Kensey et al. ................ 600/573 |
| 6,470,736 | B2 | * | 10/2002 | Price ............................ 73/54.04 |

(Continued)

FOREIGN PATENT DOCUMENTS

| | | |
|---|---|---|
| DE | 4111295 C2 | 10/1992 |
| DE | 4236407 A1 | 5/1994 |

(Continued)

OTHER PUBLICATIONS

German Search Report of DE 10 2010 039 031.3, dated Jun. 9, 2011.

*Primary Examiner* — Lisa Caputo
*Assistant Examiner* — Philip Cotey
(74) *Attorney, Agent, or Firm* — Leydig, Voit & Mayer, Ltd.

(57) ABSTRACT

A method of determining viscosity of structurally viscous fluids or beverages containing small pieces, fibers, pulps, fruit cells, cereals, particles or the like, for processing in filling, fruit juice preparation, dairy or brewery process plants, includes providing a tube rheometer having an at least substantially horizontal, straight meter tube with an inner diameter over a length of the meter tube length. At least two different volume flows are generated, exclusively gravimetrically, in the tube rheometer. The at least two different volume flows are adjusted to be substantially constant so as to determine a flow index and a consistency factor of the at least two volume flows. Pressure losses of the at least two volume flows are measured. The viscosity is determined based on the flow index, the consistency factor and the pressure losses.

5 Claims, 1 Drawing Sheet

(56) References Cited

U.S. PATENT DOCUMENTS

| | | | |
|---|---|---|---|
| 6,484,566 B1 * | 11/2002 | Shin et al. | 73/54.07 |
| 6,743,399 B1 * | 6/2004 | Weigl et al. | 422/504 |
| 6,941,797 B2 * | 9/2005 | Nowak | 73/54.07 |
| 2001/0055546 A1 * | 12/2001 | Weigl et al. | 422/100 |
| 2004/0025572 A1 * | 2/2004 | Nowak | 73/54.05 |
| 2006/0065044 A1 * | 3/2006 | Tsang et al. | 73/54.07 |
| 2008/0127718 A1 * | 6/2008 | Lesieur | 73/54.09 |
| 2009/0320568 A1 * | 12/2009 | Desie et al. | 73/54.07 |
| 2011/0219856 A1 * | 9/2011 | Tonmukayakul et al. | 73/54.01 |
| 2013/0186184 A1 * | 7/2013 | Goodall | 73/54.01 |

FOREIGN PATENT DOCUMENTS

| | | |
|---|---|---|
| DE | 102005024575 B4 | 3/2007 |
| DE | 102006001180 A1 | 9/2007 |
| EP | 0458391 A1 | 11/1991 |
| WO | WO 0239090 A2 * | 5/2002 |

* cited by examiner

METHOD AND DEVICE FOR DETERMINING VISCOSITY UTILIZING GRAVITY FEED

CROSS-REFERENCE TO PRIOR APPLICATIONS

Priority is claimed to German Patent Application No. DE 10 2010 039 031.3, filed on Aug. 6, 2010, the entire disclosure of which is hereby incorporated by reference herein.

FIELD

The present invention relates to a method and a device for determining viscosity.

BACKGROUND

For processing chunky products to be filled, such as structurally viscous fluids or beverages containing small pieces, fibers, pulps, fruit cells, particles or the like, in the beverage and food industry, in particular in processing in filling, fruit juice preparation, dairy or brewery process plants, for the calculated design of process plant equipment, such as heat exchangers, fillers, valves, and piping systems, the determination of the viscosity of the fluid or beverage to be processed, also under the influence of temperature, is extremely important, for example also to be able to assess forms of flow and residence times, and as a basis for numerical simulations and technical calculations, or as a basis for the designing of the process plant. Usually, rheometers are employed to determine the viscosity of such fluids or beverages critical with respect to the determination of their absolute viscosity, where the determination of viscosity depending on the shearing rate is reliant on a defined gap in the measuring system. These are, for example, plate/plate or cylinder/bowl systems by Searl or Couette. In these measuring systems, excessively large pieces, fibers, etc. can lead to blocking or shearing of pieces, resulting in wrong/invalid measured values. Moreover, the possibly too liquid medium in the fluids or beverages often lead to invalid measured values, in particular at higher shearing rate ranges, for example by increasing turbulences in the measuring gap, by burbling or flow fronts with eddies or inhomogeneities in the product which impede the formation of a laminar flow required for measuring. With greater shearing rates, gap emptying can also occur, in particular in case of rather long gap distances that become necessary in case of rather large particles. At lower shearing rate ranges, however, wall slip effects can occur in gap regions, leading to wrong wall shearing speeds in particular in case of rather large shearing gaps and media with yield points. Thus, incorrect torques are formed in the rheometer. These lead to invalid measured values.

Tube rheometers with a straight meter tube, a helical meter tube or an upright U-type meter tube and a pump, as well as flow control means are furthermore discussed in EP 0 458 391 A, DE 10 2005 024 575 B4, U.S. Pat. No. 5,315,863 A, DE 4111295 C2, for example for applications in ground-boring technology.

SUMMARY

In an embodiment, the present invention provides a method of determining viscosity of structurally viscous fluids or beverages containing small pieces, fibers, pulps, fruit cells, cereals, particles or the like, for processing in filling, fruit juice preparation, dairy or brewery process plants. A tube rheometer having an at least substantially horizontal, straight meter tube with an inner diameter over a length of the meter tube length is provided. At least two different volume flows are generated, exclusively gravimetrically, in the tube rheometer. The at least two different volume flows are adjusted to be substantially constant so as to determine a flow index and a consistency factor of the at least two volume flows. Pressure losses of the at least two volume flows are measured. The viscosity is determined based on the flow index, the consistency factor and the pressure losses.

BRIEF DESCRIPTION OF THE DRAWINGS

The present invention will be described in even greater detail below based on an exemplary figure. The invention is not limited to the exemplary embodiments. Other features and advantages of various embodiments of the present invention will become apparent by reading the following detailed description with reference to the attached drawings which illustrate the following.

DETAILED DESCRIPTION

Figures 1, 2:
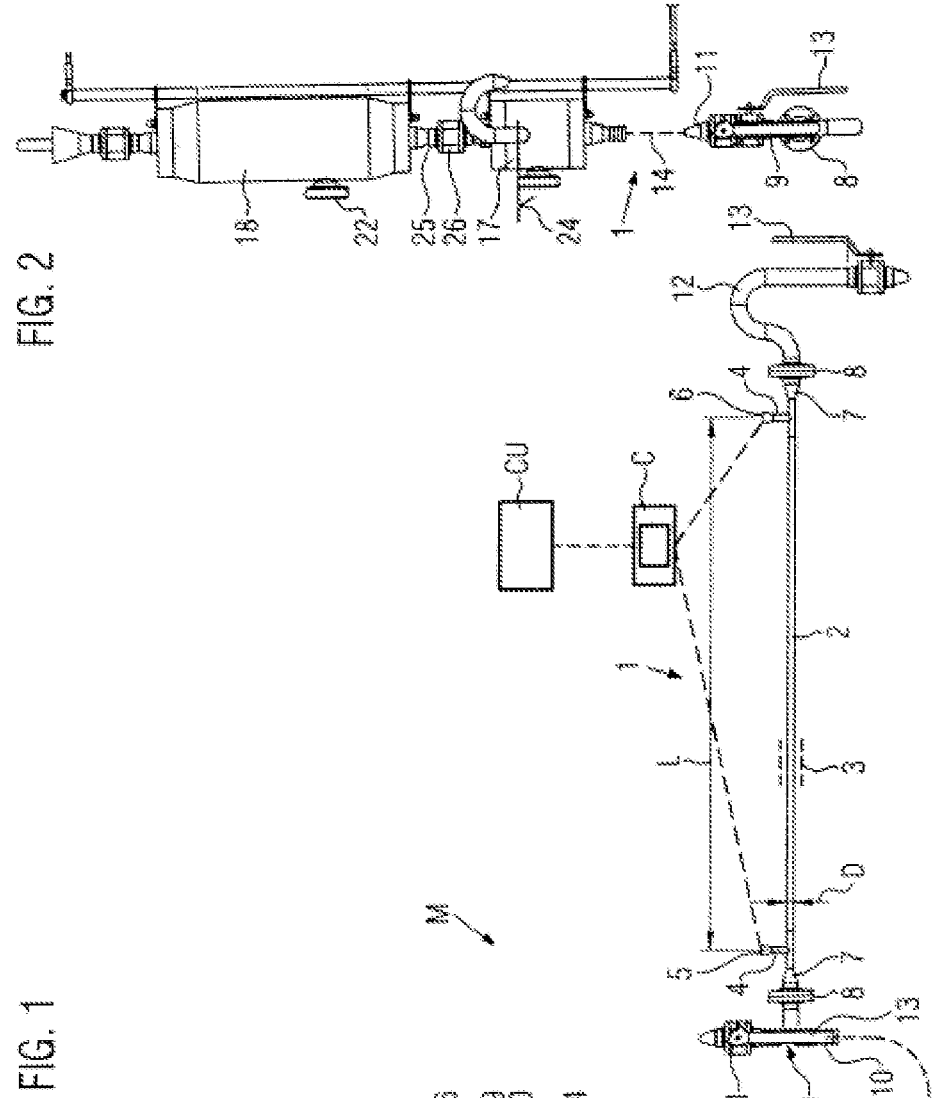
FIG. 1 shows a schematic side view of a device according to an embodiment of the present invention for determining viscosity.
FIG. 2 shows a view of the device rotated by 90°.

It has been discovered that it is still today not possible to sufficiently reliably and/or quickly determine the viscosities of the above-mentioned fluids and beverages with systems reliant on a gap.

It is an aspect of the invention to provide a method as well as a structurally simple device suited for carrying out the method by means of which the viscosity of such fluids and beverages up to now critical with respect to the determination of their viscosity can be determined quickly and reliably.

In an embodiment, the present invention provides a tube rheometer with an at least essentially horizontal, straight meter tube having a diameter over the meter tube length, and the measurement of the pressure losses and the determination of the flow index and the consistency factor from at least two different volume flows, which are adjusted to be at least largely constant and exclusively under the influence of gravity, surprisingly permit the reliable determination of the viscosity of such fluids or beverages critical with respect to the determination of their viscosity. Here, different measuring ranges can be easily covered by exchangeable meter tubes with different diameters and/or lengths, where, however, for developing the required shearing rates, extremely constant flow rates of the volume flows are adjusted exclusively gravimetrically, i.e. without a pump, whereby an acute source of falsification is removed and, among other things, the complexity of the equipment and control system is minimized. The method can be extremely flexibly employed for such fluids and beverages, can be automated and thus integrated online, and also permits the assessment of the influence on the sum viscosity and the influence of cluster or bulk flows.

The device is structurally simple and can operate without a pump that falsifies the measuring result, as the at least two volume flows are adjusted to be constant exclusively under the influence of gravity. The dosing tank is significantly responsible for a uniform flow rate during measurement, so that the viscosity of structurally viscous fluids and beverages charged with small pieces or the like of different particle concentrations can be reliably determined. The device can be employed at process plants or can be used as a mobile field test appliance and utilized universally. The device can be easily designed to be hygienically perfect and cleaned, and it can be installed at a process plant as a bypass or an outlet to a gully, while the process is running. Furthermore, the device is also equally suited for being employed in a technical school or in the laboratory.

In one suitable method variant, viscosity is determined by means of a tube rheometer by means of the model $\eta = K \cdot \gamma^{m-1}$ by Ostwald de Waele ("de Waele formula"). When at least two different volume flows are adjusted, one can determine, by means of this model, the consistency factor and the flow index with reference to measured pressure losses by which viscosity is calculated.

The method is particularly advantageous for determining the viscosity of fluids or beverages having shearing rates of up to about 1000 1/s, where the tube rheometer is designed for this shearing rate range, for example using a respectively matching meter tube from meter tubes having different dimensions.

According to the method, the respective volume flow is advantageously adjusted with at least one dosing tank positioned above the tube rheometer and is held constant during the measurement of the pressure loss, where during the measurement, a predetermined filling level is maintained in the dosing tank. The ratio of the volume flows can be up to 1:3 or more, where suitably relatively small volume flows are adjusted, for example a first volume flow of about 0.1, and a further volume flow of about 0.3 m³/h. The volume flows are preferably within the reasonable measuring range of the provided meter tube.

For an easy handling, the volume flow is adjusted by a relative height adjustment of the dosing tank and/or its filling level with respect to the meter tube.

Adjustments can be easily handled by visual inspections of the behavior of the fluid or the beverage in the dosing tank.

In an embodiment of the device, the meter tube designed for high shearing rates of up to about 1000 1/s has an L/R ratio of its length L to the radius R of the inner diameter D of more than about 100. For such fluids or beverages critical in view of the determination of their viscosity, the radius R should be, for example, at least 5 mm; for water-like, particle-charged fluids, a radius of about 10 mm is particularly suited. With this, fluids and beverages can be measured which contain particles, such as pulps, of sizes far below 1.0 mm, or oblong fibers having dimensions of 1×1×(3 mm to 5 or 10 mm to 15 or 20 mm), as well as, for example, particles of coconuts or imitations, such as nata di coco, having dimensions of 3×3×3 mm to 5×5×5/6×6×6 mm, optionally through to particle sizes of 10×10×10 mm. For fluids or beverages charged with particularly large ingredients, greater diameters and/or lengths of the meter tube can also be employed. Here, the most advantageous inner diameter as a limitation of the range of application for the admissible size of particles in the disperse media, where a D/PA ratio of about 2 to 5 is suitable, lies between the inner diameter D of the meter tube and a characteristic particle dimension PA. For valid measurements, this inner diameter depends on the total rheology and should be checked.

In an embodiment, the dosing tank comprises a filling level adjustor for keeping the filling level constant during measurement, and for changing the volume flow, either the relative height position of the dosing tank and/or the filling level in the dosing tank can be changed with respect to the meter tube. As an alternative and/or in addition, the height of the meter tube could be adjusted.

To be able to determine viscosity at the same or similar temperatures as they prevail in the process plants at certain points, it is advantageous for the meter tube to comprise a heating and is preferably contained in a heating jacket tube. A heating jacket could also be applied onto the meter tube, or the meter tube could be installed in a heating bath.

To store a dosing volume in the dosing tank with largely calm flows, it is advantageous to arrange a presettling tank upstream of the dosing tank which supplies the dosing tank. Preferably, the volume of the presettling tank is clearly greater than the volume of the dosing tank. However, it should be taken care that no flow interruptions occur between the presettling tank and the dosing tank, but that during a measuring procedure, only the constant filling level in the dosing tank is effective.

In an embodiment, the dosing tank is retained at a supporting console such that its height can be adjusted, preferably together with the presettling tank.

In an embodiment, at the presettling tank and/or the dosing tank, and/or in the region of the meter tube, ventilating means are moreover provided to be able to expel, before measurement is performed, air inclusions that falsify measurements.

In an embodiment, pressure gage sensors essentially spaced apart at a distance corresponding to the length of the meter tube are arranged at the meter tube, preferably in pressure gage tube sockets branching off from the meter tube. The pressure gage sensors can come into contact either with the fluid or the beverage, or they can be isolated from them in a pressure-transmitting manner. The pressures detected by the pressure gage sensors are evaluated along the meter tube to determine the pressure loss.

To promote uniform incoming and outgoing flow conditions in the region of the meter tube, a siphon can be provided upstream and/or downstream of the meter tube.

To facilitate visual inspection of the behavior of the fluid or beverage in the presettling tank and/or the dosing tank, an inspection glass can be provided at them, or at least regions of the tank or the tanks decisive for visual inspection are made of a transparent material.

An agitator or the like can be attached in the dosing tank and/or in the presettling tank to prevent sedimentation of non-homogenous liquids.

In order to quickly achieve very reliable measuring results adapted to an increasingly smaller shearing rate range, it is advantageous to mount the meter tube such that it can be exchanged and replaced by another one having other dimensions.

In order not to falsify or disadvantageously influence the respective volume flow through the meter tube, it can be furthermore advantageous to embody a communication connection, such as a flexible hose, from the dosing tank to the meter tube, and/or preferably at least one siphon downstream of the meter tube with an inner cross-section corresponding to a multiple of the inner cross-section defined by the inner diameter of the meter tube. For the other supply and discharge lines to the tanks and to the gully, an enlarged conduit diameter is also suitable.

A computerized evaluation means can be associated to the device which evaluates the measured values at least of the pressure gage sensors, optionally immediately calculates viscosity or, if the evaluation means is online integrated in a process plant control system, forwards the measured values with or without them being evaluated.

With respect to a universal field of employment of the device, it is advantageous to install the device either as a mobile or transportable unit, for example as a bypass or an outlet to a gully at a process plant or in a laboratory, or for it to quasi form a part of the process plant as a permanently installed unit, also as a bypass or an outlet to a gully.

The device M shown in FIGS. 1 and 2 serves to determine the viscosity of structurally viscous fluids or beverages containing small pieces, fibers, pulps, particles, fruit cells, cereals, bruised grain or the like, for example for processing in filling, fruit juice preparation, dairy or brewery process plants P according to the following method.

In a tube rheometer 1 with an at least essentially horizontal, straight meter tube 2 having a diameter D over the meter tube length L, at least two different volume flows $\dot{V}_1$, $\dot{V}_2$, are adjusted to largely constant flow rates, and by means of pressure gage sensors 5, 6, at the front end and at the end of the meter tube 2, the respective pressure difference $\Delta p$ is measured by the meter tube 2. The flow index m and the consistency factor K are determined, for example, with the model $\eta = K \cdot \dot{\gamma}^{m-1}$, the shearing rate $\dot{\gamma}_1$ being calculated for this formula according to the following formula:

$$\dot{\gamma} = \frac{4 \cdot \dot{V}}{\pi \cdot R^3},$$

where the formula $$\tau_w = \frac{\Delta p \cdot R}{2L}$$

is also employed.

For highly non-Newtonian media, the model by Rabinowitsch ("Rabinowitsch formula")

$$\dot{\gamma}_{Rab} = 0{,}75 \cdot \dot{\gamma}_s + 0{,}25 \cdot \tau_w \cdot \frac{d\,\dot{\gamma}_s}{d\,\tau_w}$$

can be used instead of the above mentioned shearing rate calculation.

To be able to determine the flow index m and the consistency factor K, where, as mentioned, the pressure losses $\Delta p_{\dot{V}_1}$, $\Delta p_{\dot{V}_2}$ for the various volume flows $\dot{V}_1$, $\dot{V}_2$ are determined, the following formulae are used:

$$\dot{V}_1 = \left(\frac{m}{3m+1}\right) \cdot \frac{\pi \cdot D^3}{8} \cdot \left(\frac{D \cdot \Delta p_{\dot{V}_1}}{4 \cdot L \cdot K}\right)^{\frac{1}{m}}$$

$$\dot{V}_2 = \left(\frac{m}{3m+1}\right) \cdot \frac{\pi \cdot D^3}{8} \cdot \left(\frac{D \cdot \Delta p_{\dot{V}_2}}{4 \cdot L \cdot K}\right)^{\frac{1}{m}}$$

The flow index m can then be determined as follows by equating the volume flows $\dot{V}_1$, $\dot{V}_2$:

$$\frac{\dot{V}_1}{\dot{V}_2} \left(\frac{\Delta p_{\dot{V}_1}}{\Delta p_{\dot{V}_2}}\right)^{\frac{1}{m}}$$

$$m = \frac{\ln\left(\frac{\Delta p_{\dot{V}_1}}{\Delta p_{\dot{V}_2}}\right)}{\ln\left(\frac{\dot{V}_1}{\dot{V}_2}\right)}$$

Subsequently, the consistency factor K is determined according to the following formula:

$$K = \left(\frac{m}{3m+1}\right)^m \cdot \frac{\pi^m \cdot D^{3m-1} \cdot \Delta p_{\dot{V}_1}}{8^m \cdot \dot{V}_1^m \cdot 4 \cdot L}$$

Finally, the viscosity $\eta$ can be calculated with the de Waele formula.

The device M in FIGS. 1 and 2 is configured such that, at the meter tube 2 with the length L and the one inner diameter D=2 R, at the front end and at the end of the length L, one measuring sensor tube socket 4 each branches off, where in the measuring sensor tube sockets, pressure gage sensors 5, 6 are mounted, which can be connected to a computerized evaluation means C, indicated in a dashed line. The evaluation means C can comprise either a display or any other representation means for the pressure loss $\Delta p$ or directly for the calculated viscosity, or it can be integrated online e.g. in a process plant control system CU.

The L/R ratio is preferably about 100 in the meter tube 2. The tube rheometer 1 is particularly well suited for determining the viscosity of fluids or beverages having shearing rates of up to about 1000 1/s. For example, the inner diameter D is 10 mm with a length L of about 1000 mm. The meter tube 2 is suitably installed such that it can be exchanged, so that it can be replaced by another one having other dimensions. In the shown embodiment, at both ends of the meter tube 2, conical connecting pieces 7 are provided which are fixed in one flanged joint 8 each so that they can be detached.

To be able to control the temperature of the fluid or beverage (heat it or cool it), the meter tube 2 can be contained in a jacket tube 3 in which a temperature control medium is flowing. As an alternative, a heating or cooling casing could be applied, or the meter tube 2 could be installed in a temperature control bath.

At the incoming side of the flanged joint 8, a fitting 9 is mounted which comprises an overhead ventilating means 11, for example with a ventilating valve and a hand lever 13, as well as a clip-on connection 10 situated at the bottom for a communication connection 14, for example a flexible hose which can be installed with an excessive length for forming a siphon 15. At the outflow side, a siphon 12 to an outlet valve follows the meter tube 2, where the outlet valve can be actuated by means of a hand lever 13. If the device M is designed as a bypass for a process plant P, the siphon 12 leads back to the process plant P. If, however, the device M is designed as an outlet to a gully G, the fluid or beverage flowing away is drained to the gully.

In the embodiment of FIGS. 1 and 2, the tube rheometer 1 includes a dosing tank 17 which is arranged above the meter tube 2, for example at a console 16, to be height adjustable. In the shown embodiment, a presettling tank 18 is arranged upstream of the dosing tank 17 and has a greater volume than the volume of the dosing tank 17, and can be filled, for example from the process plant P, via a filling device with a valve actuated by a hand lever 13. In the dosing tank 17, a filling level adjustor 19 is contained, for example in functional combination with an overflow 20. From the presettling tank 18, an overflow connection 25 leads to an immersion tube 21 and into the dosing tank 17. The filling level adjustor 19 can comprise, for example, an upright stand pipe which, in cooperation with the immersion tube 21 and the overflow 20, adjusts a certain filling level 24 (FIG. 2) in the dosing tank 17 and keeps it constant, while the fluid or the beverage follows on from the presettling tank 18, for example in a gurgling manner, however without permitting a flow interruption. In the overflow connection 25 from the presettling tank 18 to the dosing tank 17, a further valve 26 actuated by a hand lever 13 or adjustable in the flow cross-section can be contained. An integrated agitator R can be suitable as an option.

The dosing tank 17 is arranged at a height above the meter tube 2 so that a certain difference in height results between the filling level 24 in the dosing tank 17 and the meter tube 2, the difference serving to adjust and keep constant the respective determined volume flow $\dot{v}_1$, $\dot{v}_2$ through the meter tube 2 exclusively under the influence of gravity, that means gravimetrically. During measurement, the filling level 24 does not change. The filling level 24 is controlled by means of the overflow 20 and is adjusted there, for example, at its outlet in the wall of the dosing tank 17. This becomes possible as a corresponding uncoupling of flow between the dosing tank 17 and the presettling tank 18 can be effected via a selected position of the hand lever 13 or valve 26 in the overflow connection 25. To adjust another volume flow, in the shown embodiment, the height of the dosing tank 17 is adjusted at the console 16, preferably together with the presettling tank 18. In an alternative embodiment, the filling level adjustor 19, 20, 21 in the dosing tank 17 could be embodied such that the height of the filling level 24 can be changed and maintained constant again at the new adjusted level.

In the embodiment shown in FIGS. 1 and 2, the dosing tank 17 and/or the presettling tank 18 comprise inspection glasses 22. As an alternative, at least some regions of the tanks 17, 18 could consist of a transparent material.

Before a first measurement is performed, first all valves are opened to vent the dosing tank 17, as well as the communication connection 14, via the ventilating means 11, and also the meter tube 2 via the siphon 12. As soon as ventilation is completed and the fluid or beverage optionally exits at the end of the measuring path and out of the overflow 20 without air inclusions, a measuring procedure is performed with the ventilating means 11 being closed, and the pressure loss $\Delta p$ for a volume flow $\dot{v}_1$, $\dot{v}_2$ is measured. As soon as a stable measured value has been obtained, the second different volume flow $\dot{v}_1$, $\dot{v}_2$ is adjusted, for example by height adjustment of the dosing tank 17, and a second measurement of the pressure loss $\Delta p$ is performed. Viscosity is then determined as illustrated in the beginning. The respective volume flow $\dot{v}_1$, $\dot{v}_2$ can be determined by gaging the capacity by liters or by means of a sensitive flow meter.

Measurement of the pressure loss requires, for example, a sample amount of only about 5 to 10 liters.

To clean the device M, the complete flow path through the device is rinsed with a cleaning medium. Suitably, the individual components of the device M are made of hygienically perfect materials, for example mainly using stainless steel. The communication connection 14 can be used for conveying the cleaning medium and can then optionally be detached to be cleaned itself, and also to be able to clean the plug-type connections.

The meter tube 2 is fixed in a not represented mounting in which the distance between the flanged joints 8 can be optionally changed when the meter tube 2 is replaced.

The device M can be permanently installed at a process plant P, as mentioned either as an outlet or as a bypass, or as an alternative, it can be mobile or transportable and only installed for measurements. The device M can furthermore be also used in laboratories or other fields of application.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

The invention claimed is:

1. A method of determining viscosity of structurally viscous fluids or beverages containing small pieces, fibers, pulps, fruit cells, cereals or particles, for processing in filling, fruit juice preparation, dairy or brewery process plants, the method comprising:
   providing a tube rheometer having an at least substantially horizontal, straight meter tube with an inner diameter over a length of the meter tube length;
   generating, exclusively gravimetrically through the straight meter tube of the tube rheometer, at least two different volume flows of a same fluid or beverage at different times;
   adjusting the at least two volume flows each to be substantially constant so as to determine a flow index and a consistency factor of the at least two volume flows;
   measuring pressure losses of the at least two volume flows; and
   determining the viscosity based on the flow index, the consistency factor and the pressure losses.

2. The method according to claim 1, wherein the viscosity is determined by $\eta = K \cdot \gamma^{*m-1}$.

3. The method according to claim 1, wherein the tube rheometer is configured to determine the viscosity of fluids or beverages having shearing rates of up to 1000 1/s.

4. The method according to claim 1, wherein a respective one of the at least two volume flows is partially adjusted with a predetermined sample amount from at least one dosing tank disposed above the tube rheometer such that a predetermined filling level is maintained in the dosing tank during the measuring of pressure losses.

5. The method according to claim 1, wherein the at least two volume flows are adjusted by a relative height adjustment of at least one of a dosing tank disposed above the tube rheometer and a filling level of the dosing tank.

* * * * *